(12) United States Patent
Nakagawa et al.

(10) Patent No.: US 10,173,962 B2
(45) Date of Patent: Jan. 8, 2019

(54) METHOD FOR PRODUCING TRANS-RICH-1,4-BIS(AMINOMETHYL) CYCLOHEXANE

(71) Applicant: MITSUI CHEMICALS, INC., Tokyo (JP)

(72) Inventors: Aya Nakagawa, Sodegaura (JP); Tetsuya Hamada, Ichihara (JP)

(73) Assignee: MITSUI CHEMICALS, INC., Tokyo (JP)

( * ) Notice: Subject to any disclaimer, the term of this patent is extended or adjusted under 35 U.S.C. 154(b) by 0 days.

(21) Appl. No.: 15/778,147

(22) PCT Filed: Dec. 9, 2016

(86) PCT No.: PCT/JP2016/086655
§ 371 (c)(1),
(2) Date: May 22, 2018

(87) PCT Pub. No.: WO2017/099204
PCT Pub. Date: Jun. 15, 2017

(65) Prior Publication Data
US 2018/0354890 A1    Dec. 13, 2018

(30) Foreign Application Priority Data
Dec. 9, 2015 (JP) ................. 2015-240243

(51) Int. Cl.
*C07C 209/68* (2006.01)
*C07C 209/86* (2006.01)
*C07C 211/18* (2006.01)

(52) U.S. Cl.
CPC ........ *C07C 209/68* (2013.01); *C07B 2200/09* (2013.01); *C07C 2601/14* (2017.05)

(58) Field of Classification Search
CPC ... C07C 209/68; C07C 211/18; C07C 209/86; C07C 2601/14; C07B 2200/09
See application file for complete search history.

(56) References Cited

U.S. PATENT DOCUMENTS

| 3,344,164 A | 9/1967 | Seaton |
| 4,086,276 A | 4/1978 | Butte |
| 2016/0229792 A1 | 8/2016 | Yamamoto |
| 2017/0204049 A1* | 7/2017 | Yamamoto ............ C07C 209/68 |
| 2018/0044279 A1 | 2/2018 | Shimizu |

FOREIGN PATENT DOCUMENTS

| JP | S53130637 | 11/1978 |
| WO | 2015041261 A1 | 3/2015 |
| WO | 2016143539 A1 | 9/2016 |

OTHER PUBLICATIONS

PCT International Preliminary Report on Patentability (Form PCT/IB/373) filed in PCT/JP2016/086655, with PCT Notification Concerning Transmittal of International Preliminary Report on Patentability (Form PCT/IB/326) dated Jun. 21, 2018.
PCT International Preliminary Report on Patentability (Form PCT/IB/373) filed in PCT/JP2016/086655, with PCT Notification of Transmittal of Translation of the International Preliminary Report on Patentability (Form PCT/IB/338) dated Jun. 21, 2018.
International Search Report dated Jan. 10, 2017 filed in PCT/JP2016/086655.
Decision to Grant a Patent dated Mar. 14, 2017 filed in JP2017-505880; English translation.

* cited by examiner

*Primary Examiner* — Jafar F Parsa
(74) *Attorney, Agent, or Firm* — Rankin, Hill & Clark LLP

(57) ABSTRACT

The method for producing trans-rich-1,4-bis(aminomethyl)cyclohexane includes blending 1,4-bis(aminomethyl)cyclohexane with an alkali metal compound and XDA and heating the mixture to isomerize 1,4-bis(aminomethyl)cyclohexane so that the trans isomer content relative to the cis/trans isomers in total is more than 70 mass %, and purifying the isomerized 1,4-bis(aminomethyl)cyclohexane by distillation after the isomerization step. The alkali metal compound is at least one compound selected from the group consisting of alkali metal hydride, alkali metal amide, and alkyl alkali metal. In the isomerization step, 0.01 mol or more and less than 4 mol of XDA is blended relative to 100 mol of 1,4-bis(aminomethyl)cyclohexane, a dimer produced from one molecular of 1,4-bis(aminomethyl)cyclohexane and one molecular of XDA, and a trimer produced from two molecules of 1,4-bis(aminomethyl)cyclohexane and one molecular of XDA are produced, and the dimer content is 5 mass % or more and less than 75 mass % relative to the dimer and trimer in total.

5 Claims, 1 Drawing Sheet

METHOD FOR PRODUCING TRANS-RICH-1,4-BIS(AMINOMETHYL) CYCLOHEXANE

TECHNICAL FIELD

The present invention relates to a method for producing trans-rich-1,4-bis(aminomethyl)cyclohexane.

BACKGROUND ART

Conventionally, 1,4-bis(aminomethyl)cyclohexane has been well known for a material for polyamides used for, for example, fiber and film. Furthermore, 1,4-bis(isocyanatomethyl)cyclohexane derived from 1,4-bis(aminomethyl)cyclohexane is useful for a material for polyurethane used for, for example, coating, adhesive, and plastic lens.

Such 1,4-bis(aminomethyl)cyclohexane includes two stereoisomers of trans-1,4-bis(aminomethyl)cyclohexane and cis-1,4-bis(aminomethyl)cyclohexane, and cis-trans isomer ratio in 1,4-bis(aminomethyl)cyclohexane affects various physical properties of polyamide and polyurethane produced by using these.

For example, in polyamide, a higher trans isomer ratio in the material 1,4-bis(aminomethyl)cyclohexane would improve physical properties such as melting point and thermal stability, and allows for production of suitable polyamide for, for example, fiber and films.

Furthermore, in polyurethane, use of 1,4-bis(isocyanatomethyl)cyclohexane derived from 1,4-bis(aminomethyl)cyclohexane having a high trans isomer ratio as the material allows for production of polyurethane with excellent heat resistance and solubility to solvents.

Therefore, improvement in trans isomer ratio in 1,4-bis(aminomethyl)cyclohexane in various industrial fields has been examined.

For example, Patent Document 1 has proposed a method for isomerization of cyclohexanebis(methylamine). In the method, to 5.0 g of 1,4-bis(aminomethyl)cyclohexane (in the following, may also be referred to as 1,4-cyclohexanebis(methylamine)) having a trans:cis ratio of 0.5:1, 0.3 g of sodium amide and 0.2 g of para-XDA are added, and the mixture is heated at 110° C. for 5 hours (see Patent Document 1 below).

In such an isomerization method of cyclohexanebis(methylamine), 1,4-cyclohexanebis(methylamine) is isomerized to achieve a trans:cis ratio of 1:1.

CITATION LIST

Patent Document

Patent Document 1 Japanese Unexamined Patent Publication Sho 53-130637

SUMMARY OF THE INVENTION

Problem to be Solved by the Invention

However, a problem was confirmed in examination by the present inventors: the bis(aminomethyl)cyclohexane (in the following, may be referred to as cyclohexanebis(methylamine)) isomerization method described in Patent Document 1 is limited in view of improvement in the trans isomer ratio.

Thus, the present inventors have examined improvement in heating temperature and reaction time in the isomerization method described above in an attempt to improve the trans isomer ratio in 1,4-cyclohexanebis(methylamine). However, they have found that when the heating temperature and reaction time are improved in isomerization of 1,4-cyclohexanebis(methylamine), by-products increased, purification of 1,4-cyclohexanebis(methylamine) became difficult, and 1,4-cyclohexanebis(methylamine) yield reduced, and furthermore, the trans isomer yield reduced.

Thus, an object of the present invention is to provide a method for producing trans-rich-1,4-bis(aminomethyl)cyclohexane, which allows for improvement in the trans isomer content in 1,4-bis(aminomethyl)cyclohexane and the trans isomer yield, and easily purification of the isomerized 1,4-bis(aminomethyl)cyclohexane.

Means for Solving the Problem

The present invention [1] includes a method for producing trans-rich-1,4-bis(aminomethyl)cyclohexane, the method including the steps of: blending 1,4-bis(aminomethyl)cyclohexane with an alkali metal compound and xylylenediamine (in the following, referred to as XDA) and heating the mixture to isomerize the 1,4-bis(aminomethyl)cyclohexane so that the trans isomer content relative to the cis isomer and trans isomer in total is more than 70 mass %, and purifying, after the isomerization step, the isomerized 1,4-bis(aminomethyl)cyclohexane by distillation, wherein the alkali metal compound is at least one compound selected from the group consisting of alkali metal hydride, alkali metal amide, and alkyl alkali metal; in the isomerization step, 0.01 mol or more and less than 4 mol of XDA is blended relative to 100 mol of 1,4-bis(aminomethyl)cyclohexane; a dimer and a trimer are produced, the dimer (in the following, may be simply referred to as "dimer") is produced from one molecular of 1,4-bis(aminomethyl)cyclohexane and one molecular of XDA and the trimer (in the following, may be simply referred to as "trimer") is produced from two molecules of 1,4-bis(aminomethyl)cyclohexane and one molecular of XDA; the dimer content is 5 mass % or more and less than 75 mass % relative to the dimer and trimer in total.

In the method, in the isomerization step, 1,4-bis(aminomethyl)cyclohexane is blended with an alkali metal compound and XDA, and the mixture is heated. This causes 1,4-bis(aminomethyl)cyclohexane to isomerize, and produces, as by-products, a dimer produced from one molecular of 1,4-bis(aminomethyl)cyclohexane and one molecular of XDA, and a trimer produced from two molecules of 1,4-bis(aminomethyl)cyclohexane and one molecular of XDA.

Then, in the isomerization step, the above-described lower limit or more of the XDA is blended relative to 100 mol of 1,4-bis(aminomethyl)cyclohexane, and the dimer content relative to the dimer and trimer in total is the above-described lower limit or more, and therefore the trans isomer content of the 1,4-bis(aminomethyl)cyclohexane can be the above-described lower limit or more.

Furthermore, in the isomerization step, the dimer content relative to the dimer and trimer in total is the above-described upper limit or less, and therefore yield of the 1,4-bis(aminomethyl)cyclohexane (in the following, referred to as trans-rich-1,4-bis(aminomethyl)cyclohexane) having a trans isomer content of the above-described lower limit or more can be improved, and the trans isomer yield can be improved.

Furthermore, in the isomerization step, the above-described upper limit or less of the XDA is blended relative to 100 mol of 1,4-bis(aminomethyl)cyclohexane, and therefore increase in by-products (dimer and trimer) can be suppressed, and the dimer content relative to the dimer and trimer in total is the above-described upper limit or less, and therefore the trimer content relative to the dimer and trimer in total can be ensured to be the predetermined value or more.

Trimers have a high-molecular weight compared with dimers, and therefore compared with the case with dimers, difference in the boiling point can be made larger with 1,4-bis(aminomethyl)cyclohexane, and this allows for easy separation from 1,4-bis(aminomethyl)cyclohexane by distillation.

That is, in the isomerization step, increase in by-products (dimer and trimer) can be suppressed, and in the by-products, the trimer, which can be easily separated compared with the dimer, can be contained reliably to be the predetermined value or more.

With the method of the present invention, the target trans isomer (trans-1,4-bis(aminomethyl)cyclohexane) can be obtained with a relatively high dimer content, to a region of around 75 mass % of the dimer content relative to the dimer and trimer in total, with a high purification yield.

Therefore, trans-rich-1,4-bis(aminomethyl)cyclohexane can be easily and reliably separated from by-products, and trans-rich-1,4-bis(aminomethyl)cyclohexane can be purified easily.

The present invention [2] includes a method for producing the trans-rich-1,4-bis(aminomethyl)cyclohexane of [1] above, wherein in the isomerization step, 0.1 parts by mass or more and 10 parts by mass or less of the dimer and trimer in total are produced relative to 100 parts by mass of the isomerized 1,4-bis(aminomethyl)cyclohexane.

The present invention [3] includes the method for producing the trans-rich-1,4-bis(aminomethyl)cyclohexane of [1] above, wherein in the isomerization step, 0.2 parts by mass or more and 9 parts by mass or less of the dimer and trimer in total are produced relative to 100 parts by mass of the isomerized 1,4-bis(aminomethyl)cyclohexane.

With such a method, in the isomerization step, the dimer and the trimer are produced in a total within the above-described range relative to 100 parts by mass of the isomerized 1,4-bis(aminomethyl)cyclohexane, and therefore 1,4-bis(aminomethyl)cyclohexane can be reliably isomerized, and trans-rich-1,4-bis(aminomethyl)cyclohexane can be purified even more reliably.

The present invention [4] includes the method for producing the trans-rich-1,4-bis(aminomethyl)cyclohexane of [1] above, wherein in the trans-rich-1,4-bis(aminomethyl)cyclohexane, more than 70 mass % and less than 95 mass % of the trans isomer is contained relative to the cis isomer and trans isomer in total. Preferably, the upper limit value of the trans isomer content is less than 90 mass %.

Effects of the Invention

With the method for producing trans-rich-1,4-bis(aminomethyl)cyclohexane of the present invention, the trans isomer content of the 1,4-bis(aminomethyl)cyclohexane, and the trans isomer yield can be improved, and the isomerized 1,4-bis(aminomethyl)cyclohexane can be easily purified.

DESCRIPTION OF THE EMBODIMENTS

Figure 1:
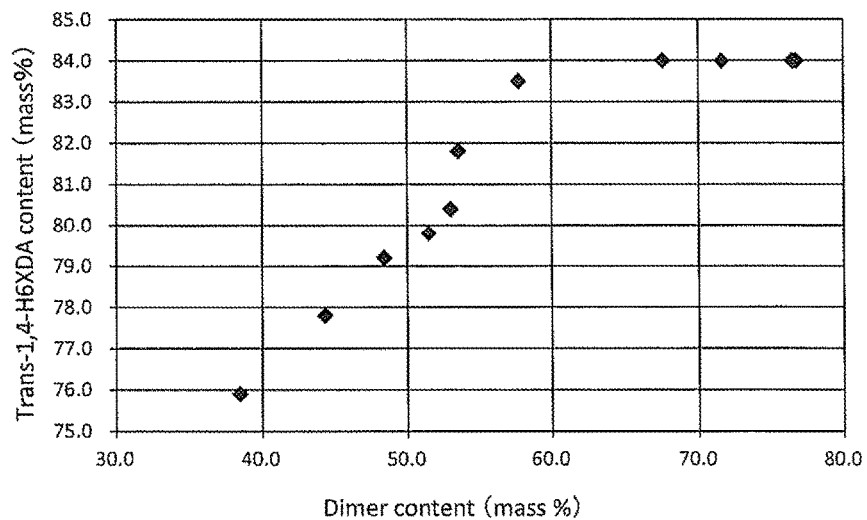
FIG. 1 is a graph illustrating the trans-1,4-bis(aminomethyl)cyclohexane content relative to the dimer content in Examples and Comparative Examples.

The method for producing trans-rich-1,4-bis(aminomethyl)cyclohexane of the present invention includes an isomerization step, in which 1,4-bis(aminomethyl)cyclohexane is isomerized, and a distillation step, in which after the isomerization step, the isomerized 1,4-bis(aminomethyl)cyclohexane is purified by distillation.

1. Isomerization Step

In this production method, first, 1,4-bis(aminomethyl)cyclohexane is prepared.

1,4-bis(aminomethyl)cyclohexane is a nuclear hydrogenation product (hydrogen adduct to benzene ring) of p-XDA, and in the following, referred to as 1,4-$H_6$XDA.

1,4-$H_6$XDA includes geometric isomers of cis isomer of 1,4-$H_6$XDA (in the following, cis-1,4-$H_6$XDA), and a trans isomer of 1,4-$H_6$XDA (in the following, trans-1,4-$H_6$XDA).

In such 1,4-$H_6$XDA, cis-1,4-$H_6$XDA content relative to the cis-1,4-$H_6$XDA and trans-1,4-$H_6$XDA in total is, for example, 30 mass % or more, preferably more than 50 mass %, more preferably 60 mass % or more, and for example, 90 mass % or less, preferably 80 mass % or less. The cis-1,4-$H_6$XDA content can be calculated by gas chromatography (GC) analysis.

That is, 1,4-$H_6$XDA prepared in the isomerization step is preferably a cis-rich-1,4-$H_6$XDA containing more than 50 mass % of cis-1,4-$H_6$XDA and less than 50 mass % of trans-1,4-$H_6$XDA.

The cis-rich-1,4-$H_6$XDA is prepared, for example, by a known method such as nuclear hydrogenation of p-XDA in the presence of a noble metal catalyst (for example, ruthenium catalyst, palladium catalyst, etc.). In this method, the isomer ratio (presence ratio under equilibrium state) of cis isomer:trans isomer is 2:1, and the cis-rich-1,4-$H_6$XDA contains about 67 mass % of cis-1,4-$H_6$XDA and about 33 mass % of trans-1,4-$H_6$XDA.

Then, 1,4-$H_6$XDA is blended with an alkali metal compound and XDA, and the mixture is heated.

The alkali metal compound is a compound of at least one selected from the group consisting of alkali metal hydride, alkali metal amide, and alkyl alkali metal.

Examples of the alkali metal hydride include sodium hydride, potassium hydride, lithium hydride, lithium aluminum hydride, and sodium borohydride.

Examples of the alkali metal amide include sodium amide, potassium amide, lithium amide, lithium diisopropylamide, and sodium bis(trimethylsilyl)amide.

Examples of the alkyl alkali metal include methyllithium, n-butyllithium, and t-butyllithium.

The alkali metal compound can be used singly, or can be used in combination of two or more.

Of the alkali metal compounds, preferably, alkali metal hydride is used, more preferably, sodium hydride is used.

The alkali metal compound is blended in an amount of, relative to 100 mol of 1,4-$H_6$XDA, for example, 1 mol or more, preferably 3 mol or more, and for example, 6 mol or less, preferably 4 mol or less.

When the alkali metal compound is blended in an amount of the above-described lower limit or more, in the isomerization step, the trans-1,4-$H_6$XDA content can be reliably improved, and when the alkali metal compound is blended in an amount of the above-described upper limit or less, the amount of the alkali metal compound used can be reduced.

Examples of XDA include m-XDA and p-XDA, and preferably, p-XDA is used. XDA can be used singly, or can be used in combination of two or more.

XDA is blended in an amount of, relative to 100 mol of 1,4-H₆XDA, 0.01 mol or more, preferably 0.1 mol or more, more preferably 0.3 mol or more, and less than 4 mol, preferably 3 mol or less, more preferably 1 mol or less.

When XDA is blended in an amount of the above-described lower limit or more, in the isomerization step, the trans-1,4-H₆XDA content can be reliably improved, and when XDA is blended in an amount of the above-described upper limit or less, excessive increase in by-products (dimer and trimer to be described later) can be suppressed.

The heating temperature (reaction temperature) can be, for example, 80° C. or more, preferably 110° C. or more, more preferably more than 110° C., particularly preferably 115° C. or more, and for example, 130° C. or less, preferably 125° C. or less, more preferably less than 120° C.

When the heating temperature (reaction temperature) is the above-described lower limit or more, in the isomerization step, improvement in trans-1,4-H₆XDA content can be effectively achieved, and when the heating temperature (reaction temperature) is the above-described upper limit or less, the dimer content to be described later can be decreased.

The pressure (reaction pressure) in the isomerization step can be, for example, 50 kPa or more, preferably 80 kPa or more, and for example, 150 kPa or less, preferably 120 kPa or less, more preferably, normal pressure.

The time (reaction time) in the isomerization step can be 2 hours or more, preferably 4 hours or more, more preferably 6 hours or more, and for example, 20 hours or less, preferably 10 hours or less, more preferably 8 hours or less.

Such an isomerization step is performed preferably under inert gas atmosphere.

Examples of the inactive gas include nitrogen, argon, and helium, and preferably, nitrogen is used. Such an inert gas can be used singly, or can be used in combination of two or more.

The isomerization step can also be performed under the presence of a reaction solvent (for example, aromatic hydrocarbons, aliphatic hydrocarbons, ethers, etc.), but preferably performed in the absence of a reaction solvent (solventless condition).

In such an isomerization step, cis-1,4-H₆XDA is isomerized into trans-1,4-H₆XDA.

For example, when the alkali metal compound is sodium hydride, and XDA is p-XDA, as shown in the formula (1) below, cis-1,4-H₆XDA is isomerized into trans-1,4-H₆XDA.

Formula (1):
[Chemical Formula 1]

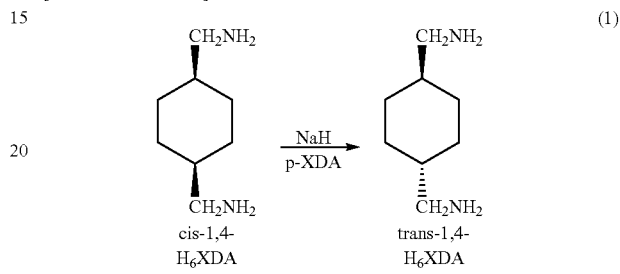

At this time, along with the isomerization shown in Formula (1) above, as by-products, a dimer produced from one molecular of 1,4-H₆XDA and one molecular of XDA, and a trimer produced from two molecules of 1,4-H₆XDA and one molecular of XDA are produced.

To be specific, first, as shown in the formula (2) below, two molecules of 1,4-H₆XDA react with one molecular of XDA to produce a trimer. Then, as shown in the formula (3) below, one molecular of 1,4-H₆XDA is eliminated from the trimer by debenzylation to produce a dimer.

Formula (2):
[Chemical Formula 2]

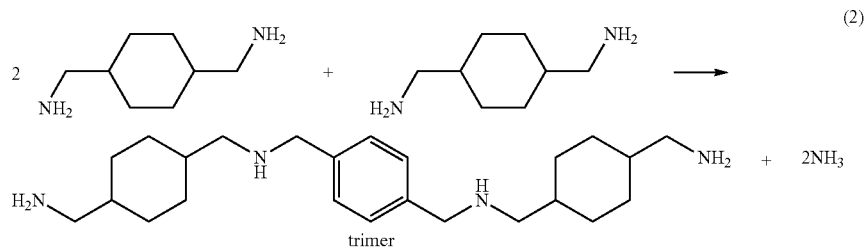

Formula (3):
[Chemical Formula 3]

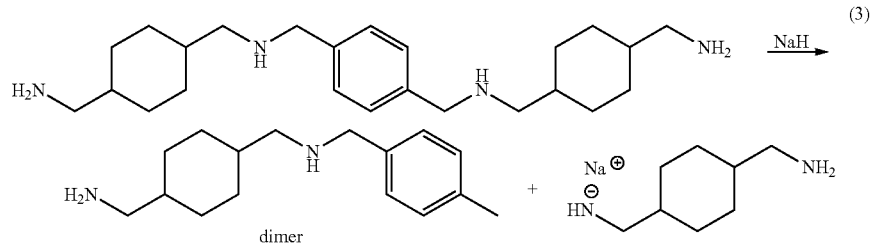

In the isomerization step, the entire amount of XDA is consumed for production of the dimer and the trimer.

The isomerization step is completed in the above-described manner, and a reaction product (reaction solution) containing cis-1,4-H$_6$XDA, trans-1,4-H$_6$XDA, dimer, and trimer is prepared.

In such a reaction product, the 1,4-H$_6$XDA yield (that is, a total of trans-1,4-H$_6$XDA and cis-1,4-H$_6$XDA relative to the 1,4-H$_6$XDA used in the isomerization step) is, for example, 80 mass % or more, preferably 90 mass % or more, and for example, 100 mass % or less, preferably 98 mass % or less.

The 1,4-H$_6$XDA yield can be calculated by, for example, quantitative analysis with an internal standard method using gas chromatography.

The cis-1,4-H$_6$XDA content relative to a total amount of reaction product is, for example, 10 mass % or more, preferably 15 mass % or more, and for example, 40 mass % or less, preferably 25 mass % or less.

The trans-1,4-H$_6$XDA content relative to a total amount of reaction product is, for example, 60 mass % or more, preferably 75 mass % or more, and for example, 90 mass % or less, preferably 85 mass % or less.

The trans-1,4-H$_6$XDA content relative to the trans-1,4-H$_6$XDA and cis-1,4-H$_6$XDA in total is more than 70 mass %, preferably 75 mass % or more, more preferably 77 mass % or more, particularly preferably 79 mass % or more, and for example, less than 95 mass %, preferably less than 90 mass %, further preferably less than 85 mass %.

The trans-1,4-H$_6$XDA yield (1,4-H$_6$XDA yield×trans-1,4-H$_6$XDA content relative to the trans-1,4-H$_6$XDA and cis-1,4-H$_6$XDA in total/100) is, for example, 68 mass % or more, preferably 70 mass % or more, more preferably 76 mass % or more, and for example, 95 mass % or less, preferably 90 mass % or less, further preferably 80 mass % or less.

The dimer content (yield) relative to a total amount of reaction product is, for example, 0.1 mass % or more, preferably 0.4 mass % or more, more preferably 0.6 mass % or more, and for example, 5 mass % or less, preferably 1 mass % or less, further preferably 0.7 mass % or less.

The dimer content relative to the dimer and trimer in total is 5 mass % or more, preferably 35 mass % or more, more preferably 40 mass % or more, particularly preferably 50 mass % or more, less than 75 mass %, preferably less than 70 mass %, further preferably 60 mass % or less, particularly preferably 58 mass % or less, especially preferably less than 57 mass %.

When the dimer content is the above-described lower limit or more, in the isomerization step, improvement in trans-1,4-H$_6$XDA content can be efficiently achieved, and when the dimer content is the above-described upper limit or less, in the distillation step described later, the trans-rich-1,4-H$_6$XDA can be easily purified.

The trimer content (yield) relative to a total amount of reaction product is, for example, 0.1 mass % or more, preferably 0.4 mass % or more, and for example, 5 mass % or less, preferably 1 mass % or less, more preferably 0.6 mass % or less.

The dimer and trimer are produced in total of, relative to 100 parts by mass of the trans-1,4-H$_6$XDA and cis-1,4-H$_6$XDA in total (isomerized 1,4-H$_6$XDA), for example, 0.1 parts by mass or more, preferably 0.2 parts by mass or more, more preferably 1.0 parts by mass or more, and for example, 10 parts by mass or less, preferably 9 parts by mass or less, more preferably 8 parts by mass or less, particularly preferably 3 parts by mass or less.

When the dimer and trimer are produced in total of the above-described lower limit or more, in the isomerization step, the trans-1,4-H$_6$XDA content can be reliably improved, and when the dimer and trimer are produced in total of the above-described upper limit or less, in the distillation step described later, the trans-rich-1,4-H$_6$XDA can be purified even more easily.

The cis-1,4-H$_6$XDA content, trans-1,4-H$_6$XDA content, dimer content, trimer content, and the dimer and trimer in total produced can be calculated by, for example, gas chromatography analysis.

2. Distillation Step

Then, reaction product is subjected to distillation. The distillation step is a step performed after the isomerization step is completed, and the isomerization step is a step that is different from the distillation step. The isomerization step and the distillation step can be performed continuously, but preferably, the isomerization step and the distillation step are individually performed by batch processing.

In the distillation step, first, as necessary, water is added to the reaction product to neutralize the alkali metal compound remained in the reaction product, and thereafter the reaction product is subjected to distillation.

Water is added in an amount relative to 100 parts by mass of the alkali metal compound used in the isomerization step of, for example, 100 parts by mass or more, preferably 200 parts by mass or more, for example, 500 parts by mass or less, preferably 300 parts by mass or less.

The reaction product can be distilled by any method without particular limitation, and single distillation can be performed, and a rectifying column can be used.

The distillation temperature is, for example, 90° C. or more, preferably 100° C. or more, for example, 150° C. or less, preferably 140° C. or less. The distillation pressure is, for example, 0 Pa or more, for example, 5 kPa or less, preferably 3 kPa or less. The distillation time is, for example, 1 hour or more, preferably 2 hours or more, for example, 20 hours or less, preferably 10 hours or less.

Examples of the rectifying column include a plate column and a packed column, and preferably a packed column is used.

Examples of the packing in the packed column include Raschig ring, Pall ring, McMahon packing, and Dixon packing, and preferably, McMahon packing is used.

When the reaction product is distilled using a rectifying column, the column bottom temperature is, for example, in the range that is the same as the above-described distillation temperature, and the column top temperature is, for example, 80° C. or more, preferably 90° C. or more, and for example, 140° C. or less, preferably 130° C. or less.

The column top pressure is, for example, in the range that is the same as the above-described distillation pressure, and the column bottom pressure is, for example, 0 Pa or more, for example, 5 kPa or less, preferably 3 kPa or less.

The reflux ratio is, for example, 1 or more, preferably 5 or more, for example, 20 or less, preferably 10 or less, and the column bottom residence time is, for example, 1 second or more, preferably 5 seconds or more, for example, 60 seconds or less, preferably 30 seconds or less.

In the above-described manner, the trans-1,4-H$_6$XDA and the cis-1,4-H$_6$XDA are distilled from the reaction product from the column top.

Therefore, as a fraction from the column top, a mixture of the trans-1,4-H$_6$XDA and cis-1,4-H-XDA can be obtained. The tank bottom (bottoms) contains the dimer and trimer.

The mixture of the trans-1,4-H$_6$XDA and cis-1,4-H$_6$XDA keeps the above-described trans-1,4-H$_6$XDA content, and is trans-rich-1,4-H$_6$XDA containing more than 70 mass % of trans-1,4-H$_6$XDA and less than 30 mass % of cis-1,4-H$_6$XDA.

The purified trans-rich-1,4-H$_6$XDA yield relative to the 1,4-H$_6$XDA used in the isomerization step is, for example, 75 mass % or more, preferably 85 mass % or more, for example, 100 mass % or less, preferably 95 mass % or less.

The trans-rich-1,4-H$_6$XDA has a purity of, for example, 95 mass % or more, preferably 98 mass % or more, and for example, 100 mass % or less.

When the trans-rich-1,4-H$_6$XDA has a purity of less than 100 mass %, the trans-rich-1,4-H$_6$XDA is a composition containing trans-rich-1,4-H$_6$XDA (cis-1,4-H$_6$XDA and trans-1,4-H$_6$XDA), and a small amount of other components (for example, dimer, trimer, etc.).

The trans-rich-1,4-H$_6$XDA is suitably used as various industrial materials, for example, as resin materials of polyurethane material and polyamide material.

For example, when it is used as the polyurethane material, the trans-rich-1,4-H$_6$XDA is derived into trans-rich-1,4-bis (isocyanatomethyl)cyclohexane by a known phosgene method or a non-phosgene method.

3. Operation and Effects

In such a method for producing trans-rich-1,4-bis(aminomethyl)cyclohexane, in the isomerization step, when 1,4-bis(aminomethyl)cyclohexane (1,4-H$_6$XDA) is blended with an alkali metal compound and XDA, and the mixture is heated, 1,4-H$_6$XDA is isomerized, and a dimer produced from one molecular of 1,4-H$_6$XDA and one molecular of XDA, and a trimer produced from two molecules of 1,4-H$_6$XDA and one molecular of XDA are produced as by-products.

In the isomerization step, XDA is blended in an amount of, relative to 100 mol of 1,4-H$_6$XDA, 0.01 mol or more, and the dimer content relative to the dimer and trimer in total is 5 mass % or more, and therefore the 1,4-H$_6$XDA trans isomer (trans-1,4-H$_6$XDA) content can be more than 70 mass %.

In the isomerization step, the dimer content relative to the dimer and trimer in total is less than 75 mass %, and therefore the yield of 1,4-bis(aminomethyl)cyclohexane (trans-1,4-H$_6$XDA) with the trans isomer content of more than 70 mass % can be improved, and the trans-1,4-H$_6$XDA yield can be improved.

In the isomerization step, XDA is blended in an amount of, relative to 100 mol of 1,4-H$_6$XDA, less than 4 mol, and therefore increase in by-products (dimer and trimer) can be suppressed, and the dimer content relative to the dimer and trimer in total is less than 70 mass %, and therefore the trimer content relative to the dimer and trimer in total can be ensured to be more than 30 mass %.

Therefore, the trans-rich-1,4-H$_6$XDA can be easily and reliably separated from by-products (dimer and trimer, etc.), and trans-rich-1,4-H$_6$XDA can be easily purified.

The distillation step is a step performed after the completion of the isomerization step, and the isomerization step is a different step from the distillation step.

However, when the isomerization step and the distillation step are simultaneously performed, XDA used in the isomerization step is distilled off along with the trans-rich-1,4-H$_6$XDA. Therefore, improvement in purity of the trans-rich-1,4-H$_6$XDA is limited.

Meanwhile, with this method, in the isomerization step, the entire amount of XDA is consumed for production of dimer and trimer, and the reaction product does not substantially contain XDA, and the distillation step is performed after the completion of the isomerization step.

Therefore, by subjecting the reaction product to distillation in the distillation step, purity of the trans-rich-1,4-H$_6$XDA can be reliably improved.

In the isomerization step, 0.1 parts by mass or more and 10 parts by mass or less, preferably 0.2 parts by mass or more and 9 parts by mass or less of the dimer and trimer are produced in total relative to 100 parts by mass of the trans-rich-1,4-H$_6$XDA, and therefore 1,4-H$_6$XDA can be reliably isomerized, and trans-rich-1,4-H$_6$XDA can be reliably purified even more.

EXAMPLES

In the following, Examples of the present invention will be described, but the present invention is not limited thereto. The specific numerical values such as blending ratio (content), property value, and parameter used in the following description can be replaced with upper limit values (numerical values defined with "or less" or "below") or lower limit values (numerical values defined with "or more" or "above") of corresponding numerical values of blending ratio (content), property value, and parameter described in the above-described "DESCRIPTION OF EMBODIMENTS". "Parts" and "%" are based on mass unless otherwise specified.

Example 1

(1) Isomerization Step

Cis-rich-1,4-bis(aminomethyl)cyclohexane (cis-rich-1,4-H$_6$XDA) having a trans isomer content of 32.2 mass % and a cis isomer content of 67.8 mass % was prepared.

Then, under nitrogen flow, a 200 mL four-neck flask equipped with a thermometer and a reflux pipe was charged with 100.03 g (0.703 mol) of cis-rich-1,4-H$_6$XDA, 0.563 g (0.0235 mol) of sodium hydride (alkali metal compound), and 0.520 g (0.00382 mol) of p-XDA, and isomerization reaction was performed at 110° C. (reaction temperature) for 8 hours (reaction time), thereby producing a reaction product.

p-XDA was blended in an amount of 0.543 mol relative to 100 mol of cis-rich-1,4-H$_6$XDA. The blending ratio of p-XDA, reaction temperature, and reaction time in Examples and Comparative Examples are shown in Table 1 and Table 2.

The reaction product contained cis isomer of 1,4-bis (aminomethyl)cyclohexane (cis-1,4-H$_6$XDA), trans isomer of 1,4-bis(aminomethyl)cyclohexane (trans-1,4-H$_6$XDA), a dimer produced from one molecular of 1,4-bis(aminomethyl)cyclohexane and one molecular of XDA (ref: above-described Formula (3)), and a trimer produced from two molecules of 1,4-bis(aminomethyl)cyclohexane and one molecular of XDA (ref: above-described Formula (2)).

(2) Distillation Step

Then, 1.26 g of water was added to 100.23 g of the reaction product to neutralize, and rectification was performed with a packed column under the following conditions.

Packing: McMahon packing (theoretical plate number 5)
Column top pressure: 0 Torr (0 Pa)
Column top temperature: 90° C.
Column bottom temperature (pot temperature): 100° C.
Reflux ratio: 5

Then, a high purity (99.99 mass %) trans-rich-1,4-H$_6$XDA was produced as a fraction. The fraction (trans-rich-1,4-H$_6$XDA) thus produced was subjected to gas chromatography analysis, and it was confirmed that the fraction contained no dimer or trimer (by-product).

Example 2 to Example 6

A reaction product and trans-rich-1,4-$H_6$XDA were produced in the same manner as in Example 1, except that the reaction temperature in the isomerization step was changed as shown in Table 1. In Example 2 to Example 6, the trans-rich-1,4-$H_6$XDA contained no dimer or trimer (by-product).

Example 7

A reaction product was produced in the same manner as in Example 6, except that in the isomerization step, the reaction time was changed to 10 hours. The trans-rich-1,4-$H_6$XDA contained no dimer or trimer (by-product).

Example 8

A reaction product and trans-rich-1,4-$H_6$XDA were produced in the same manner as in Example 3, except that in the isomerization step, the amount of p-XDA blended was changed to 2.53 g (0.0186 mol), and in the isomerization step, the reaction time was changed to 4 hours.
p-XDA was blended in an amount of, relative to 100 mol of 1,4-$H_6$XDA, 2.64 mol. The trans-rich-1,4-$H_6$XDA contained no dimer or trimer (by-product).

Example 9

A reaction product and trans-rich-1,4-$H_6$XDA were produced in the same manner as in Example 8, except that in the isomerization step, the amount of p-XDA blended was changed to 3.64 g (0.0267 mol).
p-XDA was blended in an amount of, relative to 100 mol of 1,4-$H_6$XDA, 3.80 mol. The trans-rich-1,4-$H_6$XDA contained no dimer or trimer (by-product).

Example 10

A reaction product and trans-rich-1,4-$H_6$XDA were produced in the same manner as in Example 2, except that in the isomerization step, the reaction time was changed to 10 hours. The trans-rich-1,4-$H_6$XDA contained no dimer or trimer (by-product).

Example 11

A reaction product and trans-rich-1,4-$H_6$XDA were produced in the same manner as in Example 3, except that in the isomerization step, reaction time was changed to 10 hours. The trans-rich-1,4-$H_6$XDA contained no dimer or trimer (by-product).

Example 12

A reaction product and trans-rich-1,4-$H_6$XDA were produced in the same manner as in Example 5, except that in the isomerization step, the reaction time was changed to 6 hours. The trans-rich-1,4-$H_6$XDA contained no dimer or trimer (by-product).

Example 13

A trans-rich-1,4-$H_6$XDA was produced in the same manner as in Example 5, except that in the distillation step, the reaction product was subjected to single distillation without packing. The trans-rich-1,4-$H_6$XDA contained 28 ppm of dimer. The dimer content of trans-rich-1,4-$H_6$XDA was measured by subjecting the fraction as is to gas chromatography analysis.

Example 14

A trans-rich-1,4-$H_6$XDA was produced in the same manner as in Example 9, except that in the distillation step, the reaction product was subjected to single distillation without packing. The trans-rich-1,4-$H_6$XDA contained 22 ppm of dimer.

Comparative Example 1

A reaction product was produced in the same manner as in Example 6, except that in the isomerization step, the amount of p-XDA blended was changed to 5.05 g (0.0370 mol).
p-XDA was blended in an amount of 5.27 mol relative to 100 mol of 1,4-$H_6$XDA.

Comparative Example 2

A reaction product was produced in the same manner as in Comparative Example 1, except that in the isomerization step, the reaction time was changed to 10 hours.

Comparative Example 3

A reaction product was produced in the same manner as in Comparative Example 1, except that in the isomerization step, the reaction time was changed to 6 hours.

Comparative Example 4

A reaction product was produced in the same manner as in Example 3, except that in the isomerization step, the amount of p-XDA blended was changed to 4.58 g (0.0336 mol).
p-XDA was blended in an amount of 4.78 mol relative to 100 mol of 1,4-bis(aminomethyl)cyclohexane (1,4-$H_6$XDA).

<Analysis of Reaction Product>

The reaction products produced in Examples and Comparative Examples were analyzed by gas chromatography (GC) under the following conditions.
Gas chromatography device: manufactured by Shimadzu Corporation, trade name: GC-2010 Plus
Column: manufactured by Agilent Technologies Japan, Ltd., trade name: CP-Sil CB for Amines GC Column, 30 m, 0.25 mm, 0.25 μm, 7 inch cage
Detector: manufactured by Shimadzu Corporation, trade name: FID-2010 Plus
Carrier gas: helium
Carrier gas flow rate: controlled so that column pressure was 140 kPa
Injection amount: 1.01 μL
Injection temperature: 300° C.
Split ratio: 50:1
Column temperature: 130° C. (10 min)→10° C./min→300° C. (6 min)
The trans-1,4-$H_6$XDA content relative to a total amount of 1,4-$H_6$XDA (total of cis-1,4-$H_6$XDA and trans-1,4-$H_6$XDA), the dimer yield (the dimer content relative to a total amount of reaction product), and the dimer content relative to the dimer and trimer in total were calculated based on the area % (GC area %) of the obtained GC chart.

The trimer content relative to the dimer and trimer in total, and the trimer yield (trimer content relative to a total amount of reaction product) were calculated based on the gas chromatography analysis value of XDA and dimer.

The 1,4-bis(aminomethyl)cyclohexane (1,4-$H_6$XDA) yield (selectivity coefficient) was calculated by performing quantitative analysis by internal standard method.

The trans-1,4-$H_6$XDA yield was calculated by 1,4-$H_6$XDA yield×trans-1,4-$H_6$XDA content relative to 1,4-$H_1$XDA in total/100. The results are shown in Tables 1 and 2.

Analysis results of Examples 1 to 9 and Comparative Examples 1 to 3 were plotted defining the horizontal axis as the dimer content relative to the dimer and trimer in total, and the vertical axis as the trans-1,4-$H_6$XDA content relative to a total amount of 1,4-$H_6$XDA. The results are shown in FIG. 1.

Figure 2:
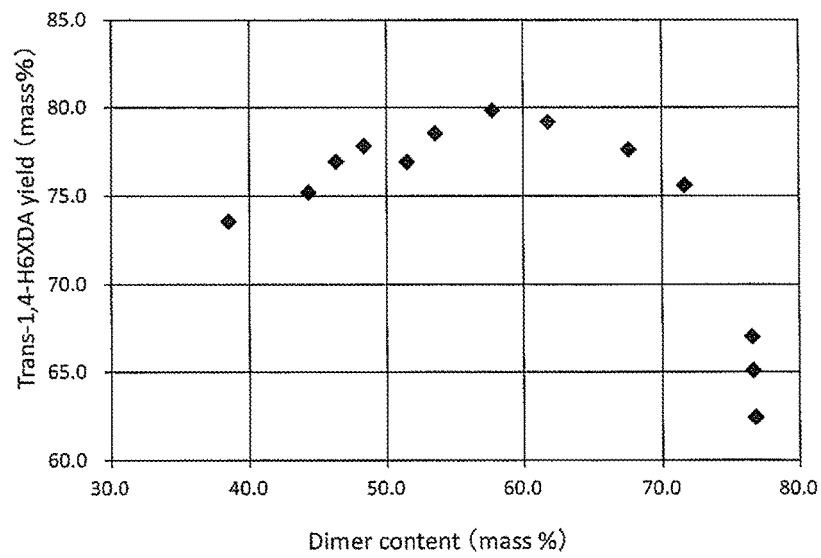
FIG. 2 is a graph illustrating the trans-1,4-bis(aminomethyl)cyclohexane yield relative to the dimer content in Examples and Comparative Examples.

The analysis results of Examples 1 to 7, 10 to 12, and Comparative Examples 1 to 3 are plotted, defining the horizontal axis as the dimer content relative to the dimer and trimer in total, and the vertical axis as the trans-1,4-$H_6$XDA yield. The results are shown in FIG. 2.

TABLE 1

|  |  | Ex. 1 | Ex. 2 | Ex. 3 | Ex. 4 | Ex. 5 | Ex.6 | Ex. 7 | Ex. 8 | Ex. 9 | Ex. 10 | Ex. 11 | Ex. 12 |
|---|---|---|---|---|---|---|---|---|---|---|---|---|---|
| Isomerization Conditions | Amount of p-XDA blended (mol relative to 100 mol of 1,4-$H_6$XDA) | 0.543 | 0.543 | 0.543 | 0.543 | 0.543 | 0.543 | 0.54.3 | 2.64 | 3.80 | 0.543 | 0.543 | 0.543 |
|  | Reaction temperature (° C.) | 110.0 | 112.5 | 115.0 | 117.5 | 120.0 | 125.0 | 125.0 | 115.0 | 115.0 | 112.5 | 115.0 | 120.0 |
|  | Reaction time (h) | 8 | 8 | 8 | 8 | 8 | 8 | 10 | 4 | 4 | 10 | 10 | 6 |
| Reaction product Composition | 1,4-$H_6$XDA yield (mass %) | 96.9 | 96.7 | 96.4 | 96.0 | 95.6 | 92.4 | 90.0 | 90.0 | 87.6 | 96.0 | 95.5 | 95.9 |
|  | Trans-1,4-$H_6$XDA content (mass % relative to cis isomer and trans isomer in total) | 75.9 | 77.8 | 79.8 | 81.8 | 83.5 | 84.0 | 84.0 | 79.2 | 80.4 | 80.1 | 81.5 | 82.6 |
|  | Cis-1,4-$H_6$XDA content (mass % relative to cis isomer and trans isomer in total) | 24.1 | 22.2 | 20.2 | 18.2 | 16.5 | 16.0 | 16.0 | 20.8 | 19.6 | 19.9 | 18.5 | 17.4 |
|  | Trans-1,4-$H_6$XDA yield (mass %) | 73.6 | 75.2 | 76.9 | 78.5 | 79.8 | 77.6 | 75.6 | 71.3 | 70.4 | 76.9 | 77.8 | 79.2 |
|  | Dimer yield (mass %) | 0.484 | 0.544 | 0.614 | 0.634 | 0.699 | 0.788 | 0.823 | 2.92 | 4.40 | 0.564 | 0.584 | 0.737 |
|  | Trimer yield (mass %) | 0.774 | 0.684 | 0.579 | 0.550 | 0.512 | 0.378 | 0.326 | 3.12 | 3.90 | 0.654 | 0.624 | 0.456 |
|  | Dimer and trimer yield in total (mass %) | 1.26 | 1.23 | 1.19 | 1.18 | 1.21 | 1.17 | 1.15 | 6.04 | 8.30 | 1.22 | 1.21 | 1.19 |
|  | Dimer and trimer produced (parts by mass relative to 100 parts by mass of 1,4-$H_6$XDA) | 1.30 | 1.27 | 1.24 | 1.23 | 1.27 | 1.26 | 1.28 | 6.71 | 9.47 | 1.27 | 1.26 | 1.24 |
|  | Dimer content (mass % relative to dimer and trimer in total) | 38.5 | 44.3 | 51.5 | 53.5 | 57.7 | 67.6 | 71.6 | 48.4 | 53.0 | 46.3 | 48.3 | 61.8 |
|  | Trimer content (mass % relative to dimer and trimer in total) | 61.5 | 55.7 | 48.5 | 46.5 | 42.3 | 32.4 | 28.4 | 51.6 | 47.0 | 53.7 | 51.7 | 38.2 |

TABLE 2

|  |  | Comp. Ex. 1 | Comp. Ex. 2 | Comp. Ex. 3 | Comp. Ex. 4 |
|---|---|---|---|---|---|
| Isomerization conditions | Amount of p-XDA blended (mol relative to 100 mol of 1,4-$H_6$XDA) | 5.27 | 5.27 | 5.27 | 4.78 |
|  | Reaction temperature (° C.) | 125.0 | 125.0 | 125.0 | 115.0 |
|  | Reaction time (h) | 8 | 10 | 6 | 8 |
| Reaction product Composition | 1,4-$H_6$XDA yield (mass %) | 77.5 | 74.3 | 79.8 | 81.0 |
|  | Trans-1,4-$H_6$XDA content (mass % relative to cis isomer and trans isomer in total) | 84.0 | 84.0 | 84.0 | 84.0 |
|  | Cis-1,4-$H_6$XDA content (mass % relative to cis isomer and trans isomer in total) | 16.0 | 16.0 | 16.0 | 16.0 |

TABLE 2-continued

|  | Comp. Ex. 1 | Comp. Ex. 2 | Comp. Ex. 3 | Comp Ex. 4 |
|---|---|---|---|---|
| Trans-1,4-$H_6$XDA yield (mass %) | 65.1 | 62.4 | 67.0 | 68.0 |
| Dimer yield (mass %) | 8.31 | 8.32 | 8.30 | 5.88 |
| Trimer yield (mass %) | 2.54 | 2.52 | 2.55 | 4.99 |
| Dimer and trimer yield in total (mass %) | 10.85 | 10.84 | 10.85 | 10.87 |
| Dimer and trimer produced (parts by mass relative to 100 parts by mass of 1,4-$H_6$XDA) | 14.00 | 14.59 | 13.61 | 13.42 |
| Dimer content mass % relative to dimer and trimer in total) | 76.6 | 76.8 | 76.5 | 54.1 |
| Trimer content (mass % relative to dimer and trimer in total) | 23.4 | 23.2 | 23.5 | 45.9 |

<Consideration>

It was confirmed that in Examples, the trans-1,4-$H_6$XDA content improved (75 mass % or more) while excessive increase in the dimer content relative to the dimer and trimer in total was suppressed (less than 75 mass %). Therefore, the trans-rich-1,4-$H_6$XDA can be easily purified while improving the trans-1,4-$H_6$XDA content, and high purity trans-rich-1,4-$H_6$XDA can be produced. Furthermore, improvement in the 1,4-$H_6$XDA yield and also improvement in the trans-1,4-$H_6$XDA yield were achieved.

Meanwhile, it was confirmed that in Comparative Examples, the dimer content excessively increased (70 mass % or more) relative to the dimer and trimer in total, and improvement in the trans-1,4-$H_6$XDA content was not achieved when the dimer content was a predetermined value or more. Therefore, the trans-1,4-$H_6$XDA content could not be efficiently improved, and purification of trans-rich-1,4-$H_6$XDA was difficult.

It was confirmed that in Comparative Examples 1 to 3, the 1,4-$H_6$XDA yield and the trans-1,4-$H_6$XDA yield decreased.

While the illustrative embodiments of the present invention are provided in the above description, such is for illustrative purpose only and it is not to be construed as limiting in any manner. Modification and variation of the present invention that will be obvious to those skilled in the art is to be covered by the following claims.

INDUSTRIAL APPLICABILITY

A method for producing trans-rich-1,4-bis(aminomethyl) cyclohexane of the present invention is suitably used for production of 1,4-bis(aminomethyl)cyclohexane used for various industrial materials, for example, resin materials such as polyurethane material and polyamide material.

The invention claimed is:

1. A method for producing trans-rich-1,4-bis(aminomethyl)cyclohexane, the method comprising the steps of:
    blending 1,4-bis(aminomethyl)cyclohexane with an alkali metal compound and xylylenediamine and heating the mixture to isomerize 1,4-bis(aminomethyl)cyclohexane so that the trans isomer content relative to the cis isomer and trans isomer in total is more than 70 mass %,
    purifying, after the isomerization step, the isomerized 1,4-bis(aminomethyl)cyclohexane by distillation,
    wherein the alkali metal compound is at least one compound selected from the group consisting of alkali metal hydride, alkali metal amide, and alkyl alkali metal,
    in the isomerization step,
        0.01 mol or more and less than 4 mol of xylylenediamine is blended relative to 100 mol of 1,4-bis(aminomethyl)cyclohexane, and
    a dimer and a trimer are produced,
        wherein the dimer is produced from one molecular of 1,4-bis(aminomethyl)cyclohexane and one molecular of xylylenediamine, and
        the trimer is produced from two molecules of 1,4-bis(aminomethyl)cyclohexane and one molecular of xylylenediamine, and
    the dimer content is 5 mass % or more and less than 75 mass % relative to the dimer and trimer in total.

2. The method for producing trans-rich-1,4-bis(aminomethyl)cyclohexane according to claim 1,
    wherein in the isomerization step, 0.1 parts by mass or more and 10 parts by mass or less of the dimer and trimer in total are produced relative to 100 parts by mass of the isomerized 1,4-bis(aminomethyl)cyclohexane.

3. The method for producing trans-rich-1,4-bis(aminomethyl)cyclohexane according to claim 1,
    wherein in the isomerization step, 0.2 parts by mass or more and 9 parts by mass or less of the dimer and trimer in total are produced relative to 100 parts by mass of the isomerized 1,4-bis(aminomethyl)cyclohexane.

4. The method for producing trans-rich-1,4-bis(aminomethyl)cyclohexane according to claim 1,
    wherein in the trans-rich-1,4-bis(aminomethyl)cyclohexane, more than 70 mass % and less than 95 mass % of the trans isomer is contained relative to the cis isomer and trans isomer in total.

5. The method for producing trans-rich-1,4-bis(aminomethyl)cyclohexane according to claim 1,
    wherein in the trans-rich-1,4-bis(aminomethyl)cyclohexane, more than 70 mass % and less than 90 mass % of the trans isomer is contained relative to the cis isomer and trans isomer in total.

* * * * *